United States Patent [19]
Hodge

[11] Patent Number: 4,461,296
[45] Date of Patent: Jul. 24, 1984

[54] SURGICAL SAW BLADE

[76] Inventor: Joseph Hodge, 856 N. Church St., Spartanburg, S.C. 29303

[21] Appl. No.: 30,693

[22] Filed: Apr. 16, 1979

[51] Int. Cl.³ .............................................. A61B 17/14
[52] U.S. Cl. ........................................ 128/317; 30/347
[58] Field of Search ...................... 128/317, 305, 91 A; 30/390, 388, 166 R, 347

[56] References Cited
FOREIGN PATENT DOCUMENTS
215411  7/1968  U.S.S.R. ............................... 128/317

Primary Examiner—Michael H. Thaler
Attorney, Agent, or Firm—Wellington M. Manning, Jr.; Luke J. Wilburn, Jr.

[57] ABSTRACT

A saw blade is adapted for attachment to a power operated surgical saw having a blade element with teeth disposed along at least a portion of the periphery of same to define a cutting surface and having a saw connector receiving opening therein. A guard element is secured to the blade portion on at least one side thereof and extends outwardly therefrom in a direction transverse to the major axis of the blade. The guard portions are set at a predetermined distance from the cutting surface so as to define a depth of cut of the saw blade, whereby a surgeon may utilize the blade, either rotary type, or oscillatory type for sternal splitting incisions without the danger of too deep a cut to a point where injury to the heart and great vessels can occur. Likewise, blades according to the present invention can be utilized with greater safety for the patient in removal of casts and for orthopedic surgical purposes.

4 Claims, 6 Drawing Figures

SURGICAL SAW BLADE

BACKGROUND OF THE INVENTION

Various and sundry techniques have been utilized heretofore by surgeons in performing sternal splitting incisions on a patient to permit operative access to internal organs within the chest cavity, and particularly to approach the auterior, superior or posterior mediastinum for removal of lesions of the thymus, explorations for parathyroid adenoma, and approaching the heart for modern open heart procedures. After making a sternal incision, either median or transverse the rib cage can then be separated to provide the necessary access. In making the cut, the surgeon has historically been forced to utilize his own judgment as to the depth of the cut, attempting to avoid contact with any internal organs or great vessels that could be adversely affected by severance. As such, blades rotary in nature and reciprocatory or oscillatory in nature have been utilized with power operated surgical saws. In addition, and as a primary tool, due to the safety hazards involved, surgeons have utilized a manual blade such as the Lebiske knife which, after incision at a point just above the sternum, can be inserted with a curved tip of the blade resting beneath and against the sternum. While lifting the curved blade to attempt to raise the rib cage off internal body organs, the surgeon can strike a surface of the blade with a further tool to drive the blade through the sternum and open the chest cavity.

Obviously, all the techniques described above are fraught with problems and danger to the patient. For example, incident to use of the normal rotary or oscillatory blades of the prior art which do not possess guard elements, the surgeon must very carefully use same to avoid a downward surge into the mediastinum once the sternum has been completely severed. Such practices must be very tediously followed since the marrow cavity varies with the age and size of the patient. Likewise the size of the individual, physical abnormalities and the like may vary location of the internal body organs. The adult sternum measures between 1 centimeter and 2.5 centimeters with an average depth from the outer table through the marrow cavity and inner table approximating 1.5 centimeters. With infants or small children the operative procedures become still more delicate than with adults due to location of the internal body organs and the ever present danger of reaching same with a power saw. Utilizing manual techniques, a greater stress is obviously placed on the surgeon during the actual operation procedures. Likewise, since the curved tip Lebiske knife is utilized and must be physically driven through the bone, the actual cut is not nearly as neat as when accomplished by a rotary or oscillatory blade, the patient suffers greater possible trauma and likewise there is an ever present danger of causing further damage to the rib cage due to the possibility of fracture of adjacent bones prompted by forces applied to the knife.

Surgical saw blades of the present invention minimize, if not alleviate, the problems set forth above, in that the blades may now be provided with a guard means extending outwardly from at least one side thereof, the particular location of which defines the precise depth of cut that is permitted. The need for manual procedures is thus normally eliminated and the rotary or reciprocatory surgical saw blades may be utilized with a much higher degree of precision whereby the possibility of damage to internal body organs and great vessels is substantially lessened. Blades of the present invention are particularly useful on patients undergoing secondary open heart surgery since the auterior mediastinum of the patient can be markedly reduced in size as a result of the previous surgery, making the heart and great vessels more vulnerable to injury.

SUMMARY OF THE INVENTION

It is an object of the present invention to provide an improved surgical saw blade for use in conjunction with a power operated surgical saw, which blade is designed to permit a cut of a predetermined depth only.

Another object of the present invention is to provide an improved surgical saw blade that may be used in opening the chest cavity of a patient, following midline or transverse techniques without danger of inadvertently severing vital body organs or parts.

Yet another object of the present invention is to provide an improved rotary surgical saw blade for use in conjunction with a power operated surgical saw.

Still another object of the present invention is to provide an improved oscillatory surgical saw blade for use in conjunction with a power operated surgical saw.

Still further, another object of the present invention is to provide an improved rotary saw blade for use in conjunction with a power saw with different portions of the blade permitting different depths of cut.

Generally speaking, the present invention relates to an improved surgical saw blade for attachment to a power operated surgical saw comprising a blade portion, said blade portion having teeth disposed along at least a portion of an outer periphery of same and defining a cutting surface thereat, said blade portion further having a saw connector receiving opening therethrough for securement of said blade to said saw, and a guard element provided on at least one side of said blade portion, being located at a predetermined distance from said cutting teeth and extending outwardly from said blade in a direction transverse to a major axis therethrough, said guard element being sufficient in length to preclude ingress of said cutting teeth beyond a cutting depth defined by the distance between said cutting teeth and said guard element.

More specifically, the surgical saw blade, according to the teachings of the present invention, are provided to permit surgeons to use same during operative procedures without the danger of severing internal body parts or organs during the opening of a chest cavity. Such preventive measures are achieved by the guard element located on at least one side of the saw blade and extending outwardly therefrom, said element being positioned at a predetermined distance from the saw teeth and being sufficient in length to preclude ingress of the teeth beyond the predetermined distance.

In certain embodiments, the guard elements are preferably provided on opposite sides of the blade of the present invention. Likewise, the guard element may be symmetrical and concentrically located with respect to the center of the blade to provide a constant limitation to the length of cut, or may be eccentric and/or nonsymmetrical whereby in an oscillating use, different portions of the blade are capable of different depths of cut.

Surgical saw blades of the present invention may likewise be employed for removing rigid casts and the like where the blade is designed for a cutting depth which avoids contact with the body limb or portion that is encompassed by the cast. While present blades for removing casts are designed to avoid cutting the skin, blades according to the present invention would preclude skin burns and other discomfort caused by contact of the prior art blades with the skin.

DESCRIPTION OF PREFERRED EMBODIMENTS

Figure 1:
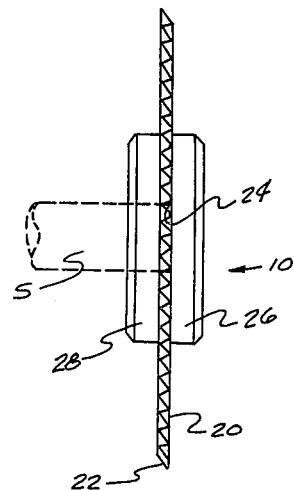
FIG. 1 is an end elevational view of a surgical saw blade according to the teachings of the present invention.
Figure 2:
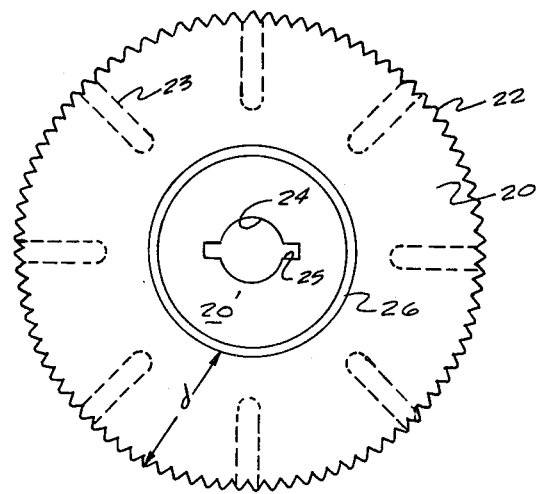
FIG. 2 is a side elevational view of the surgical saw blade as set forth in FIG. 1.

Referring to the Figures, preferred embodiments of the present invention will now be described in detail. In FIGS. 1 and 2, one embodiment of a surgical saw blade according to teachings of the present invention is illustrated, that being a rotary blade that is adapted for attachment to a power operated rotary surgical saw, such as the Zimmer power saw. A blade generally indicated as 10 is provided having a blade portion 20 that is circular in shape and has a plurality of cutting teeth 22 located around the outer periphery thereof. As illustrated in FIG. 2, cutting teeth 22 may be disposed completely around the periphery of blade 20 or as indicated in broken lines, the cutting section may be interrupted periodically by radially extending slots 23 which are provided to receive bone cuttings and thus improve the overall efficiency of the cutting operation. Slots 23, when utilized, are normally provided at spaced apart locations totally around the periphery of the circular blade 20.

Circular blade 20 is further provided with a generally circular shaped opening 24 at a central location therethrough with a pair of slots 25 extending outwardly from opposite sides of same, all of which defines a connector receiving opening into which a portion of the power operated saw, indicated in phantom in FIG. 1, may be received for securement of blade 10 to the saw. Since the power operated surgical saw is a standard item and is not considered a part of the present invention, same is not illustrated herein.

Blade portion 20 is provided with guard elements 26 and 28 located at opposite sides of same and extending outwardly therefrom in a direction transverse to a major axis through blade portion 20. Guard elements 26 and 28 are symmetrical and are located concentrically with respect to the center of blade 10. Guard elements 26 and 28 may be individual elements that are physically secured by welding or the like to opposite sides of a blade 20, or may be a single element that passes through an opening in blade 20 to receive same. In the event a single element is provided, obviously the blade portion 20' located within guard elements 26 and 28 would be a separate element which would in turn be secured within the annular space defined by guard elements 26 and 28 and properly secured therein. In like vein, the blade illustrated in FIGS. 1 and 2 may be provided with only one guard element protruding from only one side of the blade.

Guard elements 26 and 28 should extend outwardly from blade portion 20 for a sufficient distance that portions of same will engage opposite sides of an incision of the patient and preclude further ingress of the cutting element into the affected body portion. In like fashion, since the particular use of the blade 10 may determine the necessary depth of the cut, and since the physical makeup of the patients may vary as to location or depth of body organs or parts to be avoided during cutting, the distance d (See FIG. 2) between the outer edge of the cutting teeth 22 and the outer edge of the guard elements 26 and 28 may be set at various predetermined distances.

The circular blade 10 generally is provided with the guard elements 26 and 28 located at distances of 0.9, 1.2 or 1.5 centimeters from the cutting edge of the blade. Further guard elements 26 and 28 are preferably approximately 1 centimeter in length. Hence as the blade 10 is used with a power saw to traverse the patient's outer table and marrow cavity and thus penetrate the inner table, guard elements 26 and 28 extend one centimeter to each side of blade 20 and come to rest on the outer table of the sternum, preventing penetration and consequent possible injury to the great vessels of the mediastinum and heart.

Figure 3:
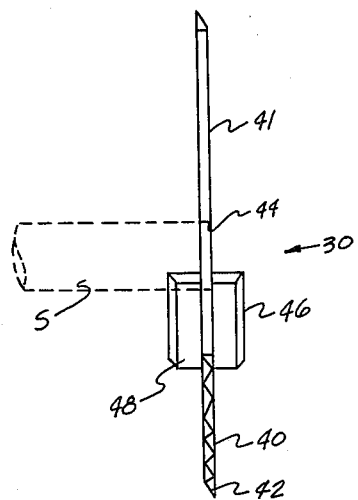
FIG. 3 is an end elevational view of a further surgical saw blade according to teachings of the present invention.
Figure 4:
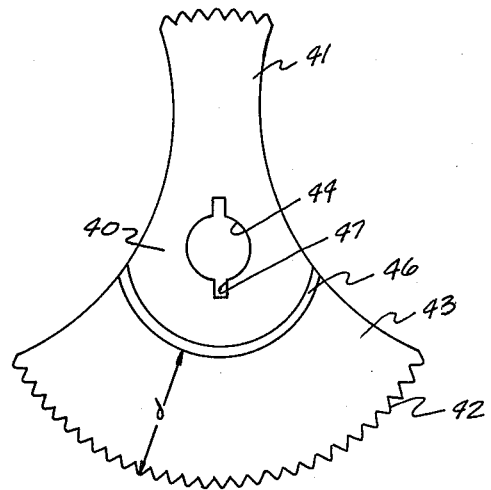
FIG. 4 is a side elevational view of the saw blade as illustrated in FIG. 3.

FIGS. 3 and 4 illustrate a further embodiment of the improved saw blade according to teachings of the present invention wherein, a purely oscillating blade generally indicated as 30 is provided. As shown in FIGS. 3 and 4, a blade portion 40 is provided having cutting teeth 42 located along a particular arcuate section 43 of same to define a cutting surface therealong. Blade 30 at the terminal portions of arcuate section 43 extends rearwardly in concave fashion to define a counterbalance blade section 41. Oscillatory blade 30 is provided with a saw connector receiving opening 44, likewise having rectangular slots or extensions 47 extending outwardly from opposite sides of same, whereby a shaft or the like S (See FIG. 3) may be received therein to connect same to a power operated oscillating surgical saw such as a Stryker saw (not shown). Guard elements 46 and 48 are provided along arcuate section 43 of blade portion 40, being secured to opposite sides of same and extending outwardly in a transverse direction to the major axis of the blade. Guard elements 46 and 48 are generally like those as described with references to FIGS. 1 and 2, in that, they are provided to contact the outer table of the sternum and thus limit a particular cutting depth d for blade 30 depending upon the intended use of the blade, whereby the blade may be safely utilized without danger of severing important body organs or parts. In like fashion to FIGS. 1 and 2, guard elements 46 and 48 may be separate elements secured to opposite sides of blade portion 40 or may be a single element that extends through blade portion 40. Likewise, only one of the guard elements may be employed.

Figure 5:
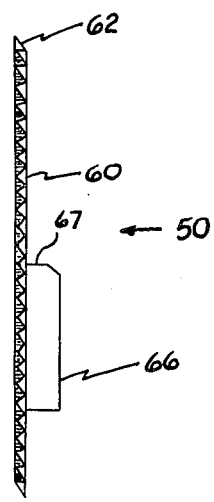
FIG. 5 is an end elevational view of a further embodiment of the present invention, illustrating a single oscillatory blade having different cut depth limitations thereon.
Figure 6:
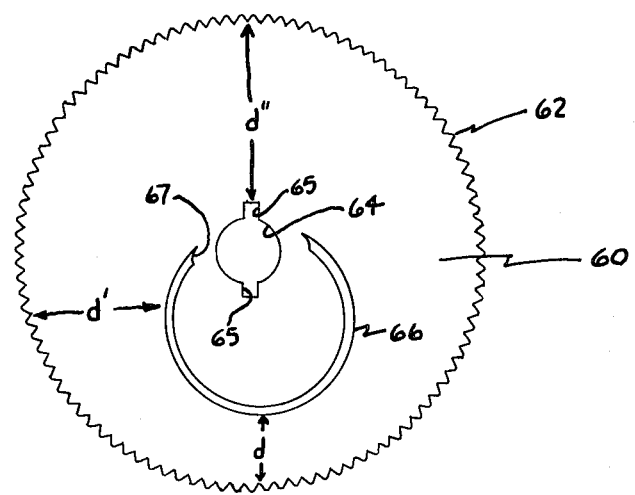
FIG. 6 is a side elevational view of the blade as illustrated in FIG. 5.

A further embodiment of a surgical saw blade according to teachings of the present invention will be described with respect to FIGS. 5 and 6. A blade generally indicated as 50 is provided having a circular body portion 60 with a plurality of cutting teeth 62 located around the periphery of same. Blade body 60 is further provided with a central circular shaped opening 64 with a pair of slots 65 extending outwardly from opposite sides of same, by which blade 50 is secureable to a power operated saw. As discussed below, blade 50 is preferably designed for use with an oscillatory saw such as a Stryker saw (not shown).

A guard element 66 is provided on one side of blade body 60, being appropriately secured thereto as mentioned above. Guard element 66 as opposed to the guard elements 26 and 28 of FIGS. 1 and 2 is neither concentrically located with respect to the center of blade body 60 nor symmetrical. Instead, guard element 66 is eccentric to the center of blade body 60 and, though illustrated as generally circular in appearance, terminates at ends 67 adjacent opening 64. With guard element 66 so provided, it becomes apparent that the depth of cut at d along one portion of blade 50 is substantially less than the depth of cuts at d', d", etc. along other portions of blade 50. Hence, a surgeon needing to make a deeper cut than is possible at d could simply use the portion of blade 50 at d', d" etc. This particular embodiment thus affords a variable possible cut depth for a single blade.

As shown in the drawings, guard element 66 extends outwardly from blade 50 a distance less than the length of the cutting surface. The length of the cutting surface is defined as the distance that teeth 62 extend around the periphery of blade 50.

Having described the invention in detail as to preferred embodiments, it is obvious that certain modifications or alterations may be made thereto without departing from the scope of the present invention. The scope of the present invention should thus be determined by the claims appended hereto.

That which is claimed is:

1. An improved surgical saw blade for attachment to a power operated surgical saw comprising a blade portion having teeth disposed along at least a portion of an outer periphery of same and defining a cutting surface thereat, said blade portion further defining a saw connector receiving opening centrally therethrough for securement of said blade to said saw, and an arcuate guard element secured directly to a side of said blade portion, and extending outwardly from said blade portion in a direction transverse to a major axis through said blade portion defining the width of the guard element, said width being sufficient to preclude ingress of said cutting teeth beyond a cutting depth defined by the distance between said cutting teeth and a surface of said guard element closest said teeth, the width of the guard element being less than the length of the cutting surface said guard element being located with respect to said cutting teeth to define various cut depths along the length of the cutting surface whereby a surgeon using same may achive a predetermined cut depth by presentation of a predetermined portion of said blade to a surface to be cut.

2. A saw blade as defined in claim 1 wherein said blade portion is circular.

3. A saw blade as defined in claim 1 wherein said opening is generally circular in shape with oppositely positioned elongated slots extending outwardly therefrom.

4. A saw blade as defined in claim 1 wherein said blade portion has a plurality of specially separate elongated slots extending from said outer periphery radially inwardly, said slots being located along said cutting surface.

* * * * *